United States Patent [19]

Pendri et al.

[11] Patent Number: 5,892,106
[45] Date of Patent: Apr. 6, 1999

[54] PREPARATION OF 3-FLUORO OXINDOLE DERIVATIVES

[75] Inventors: Yadagiri R. Pendri, Matawan, N.J.; Eduardo J. Martinez, Lakewood, Calif.; John K. Thottathil, Princeton, N.J.; Piyasena Hewawasam, Middletown, Conn.

[73] Assignee: Bristol-Myers Squibb Company, Princeton, N.J.

[21] Appl. No.: 99,472

[22] Filed: Jun. 18, 1998

Related U.S. Application Data

[62] Division of Ser. No. 946,393, Oct. 7, 1997, Pat. No. 5,808,095.

[60] Provisional application No. 60/048,218, May 30, 1997 and provisional application No. 60/027,543, Oct. 15, 1996 and provisional application No. 60/028,296, Oct. 11, 1996.

[51] Int. Cl.[6] .................................................. C07C 205/06
[52] U.S. Cl. ............................................. 562/435; 560/21
[58] Field of Search ................................ 560/21; 562/435

[56] References Cited

U.S. PATENT DOCUMENTS 5,565,483  10/1996  Hewawasam et al. ................ 514/411
5,602,169  2/1997   Hewawasam et al. ................ 514/418

*Primary Examiner*—Zinna Northington Davis
*Attorney, Agent, or Firm*—Aldo A. Algieri

[57] ABSTRACT

The present invention relates to novel intermediates of the formula

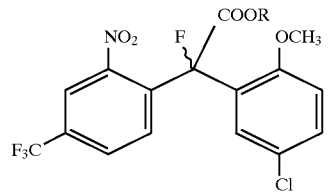

wherein the wavy bond (∿) represents the racemate, the (R)-enantiomer or the (S)-enantiomer; and R is hydrogen, a carboxyl-protecting group or a cation of an addition salt; or solvate thereof; and to the use thereof in a process for the preparation of certain 3-fluoro oxindole derivatives.

9 Claims, No Drawings

PREPARATION OF 3-FLUORO OXINDOLE DERIVATIVES

CROSS-REFERENCE TO RELATED APPLICATIONS

This is a divisional application of application U.S. Ser. No. 08/946,393 filed Oct. 7, 1997, now U.S. Pat. No. 5,808,095 which claims the benefit of copending provisional applications, U.S. Ser. No. 60/048,218 filed May 30, 1997, U.S. Ser. No. 60/027,543 filed Oct. 15, 1996, and U.S. Ser. No. 60/028,296 filed Oct. 11, 1996.

FIELD OF THE INVENTION

The present invention provides novel intermediates and processes for the preparation of 3-fluoro oxindole derivatives which are modulators of the large-conductance calcium-activated potassium (Maxi-K) channels and, therefore, useful in the protection of neuronal cells, especially in the treatment or prevention of ischemic stroke. The present invention also provides a simple and convenient chiral process for the preparation of the 3-fluoro oxindoles and to certain chiral intermediates thereof.

BACKGROUND OF THE INVENTION

A number of 3-aryl substituted oxindole compounds are described by P. Hewawasam et al. in U.S. Pat. Nos. 5,565,483 and 5,602,169, issued Oct. 15, 1996 and Feb. 11, 1997, respectively, which are useful for the treatment of disorders responsive to modulation of the large conductance calcium-activated (Maxi-K) channels, and having the general formula

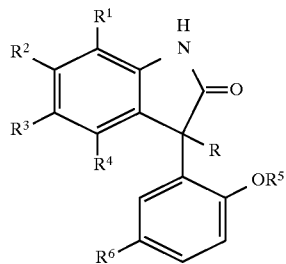

wherein R is defined as hydrogen, hydroxy or fluoro. The compounds described by P. Hewawasan et al. are generally prepared by well-known procedures employing the use of isatins as intermediates. An alternative route via cyclization of an anilino-ester intermediate for the preparation of compounds wherein R is hydrogen is also described.

Since the general method produces a racemic mixture of compounds, there is also described a method for the stereospecific insertion of a 3-hydroxy moiety via selective oxidation with the appropriate chiral oxidizing agent to provide compounds having the (3R) or (3S) configuration. However, in the instance wherein R is fluoro and the fluorination is carried out with diethylaminosulfur trifluoride (DAST) a racemic mixture of 3-fluoro 3-aryl substituted oxindoles are described and separation of the enantiomeric forms of the compound is achieved by the separation of the racemic mixture using high pressure liquid chromatography. The separation of enantiomers by chiral column chromatography is not an efficient process, especially on a commercial scale for the preparation of a single enantiomer.

The present inventors have now found a simple, convenient and economical chiral process for the preparation of substantially pure enantiomers of 3-fluoro substituted 3-aryl oxindoles and to certain chiral intermediates thereof.

SUMMARY OF THE INVENTION

The present invention provides a novel process for the preparation of an oxindole compound of the formula

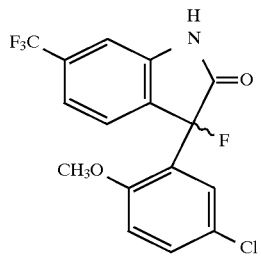

wherein the wavy bond (~) represents the racemate, the (R)-enantiomer or the (S)-enantiomer using certain novel racemic and chiral fluoro-substituted intermediates and to a process for their preparation.

DETAILED DESCRIPTION OF THE INVENTION

The present invention provides novel racemic and chiral intermediates which are useful for the preparation of certain modulators of the large-conductance calcium-activated potassium (Maxi-K) channels described herein, and which have the formula

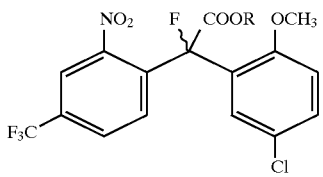

wherein the wavy bond (~) represents the racemate, the (R)-enantiomer or the (S)-enantiomer; and R is hydrogen, a carboxyl-protecting group or a cation of an addition salt; or solvate thereof.

The present invention also provides processes for the preparation of compounds of Formula IV and to processes for the preparation of 3-fluoro oxindole derivatives of the formula

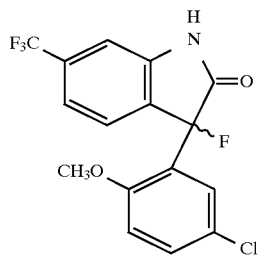

wherein the wavy bond (~) represents the racemate, the (R)-enantiomer or the (S)-enantiomer.

The term "$C_{1-6}$ alkyl" and "$C_{1-4}$ alkyl" as used herein and in the claims (unless the context indicates otherwise) mean straight or branched chain alkyl groups such as methyl, ethyl, propyl, isopropyl, butyl, isobutyl, t-butyl, amyl, hexyl, and the like. Most preferably, these groups contain 1 or 2 carbon atoms.

The term "a cation of an addition salt" as used herein and in the claims is intended to include alkali metal salts such as sodium, potassium, calcium and magnesium, the ammonium salt, salts with non-toxic amines such as trialkylamines, pyridine, picoline, dibenzylamine, ethanolamine, N-methylmorpholine, N-methylglucamine, lysine, arginine, salts with optically active salt-forming agents described herein, and other amines which have been used to form salts of carboxylic acids.

Suitable reducing agents which can be employed in the present invention are reducing agents which effectively reduce the nitro group to an amino group without affecting other functional groups. Reducing agents such as sodium dithionite, iron in acetic acid and the like are preferred.

The term "wavy bond (⸺)" which is attached to a fluorine atom as used herein in the chemical structures and in the claims is intended to include the racemic mixture as well as the two individual stereoisomers designated herein as (R)-enantiomer and (S)-enantiomer. It should be appreciated by those skilled in the art that this definition applies equally to the cyclic 3-fluoro oxindole compounds as well as the acyclic α-fluoro benzeneacetic acid compounds. The term "straight bond (—)" which is attached to a fluorine atom as used herein in the chemical structures and in the claims (unless the context or chemical structure indicates otherwise) means a racemic mixture.

As the compounds of the present invention possess an asymmetric carbon atom at the 3-position of the oxindole ring, the present invention includes the process for the preparation of the racemate as well as the individual enantiometric forms of the compounds of Formula I as described herein and in the claims. The use of a single designation such as (R) or (S) is intended to include mostly one stereoisomer. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. Although the enantiomeric forms may be separated by fractionation through chiral high pressure liquid chromatography columns, the optically active enantiomers of the compounds of Formula I are preferably prepared by stereoselective synthetic procedures described herein. The use of optically active reagents in combination with the appropriate intermediate of Formula V described herein is the preferred method to produce the desired enantiomer of the compound of Formula I.

Certain of the intermediates of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

Carboxyl-protecting groups which can be employed in the present invention to block or protect the carboxylic acid function are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Examples of such readily removable carboxyl-protecting groups include moieties such as $C_{1-6}$ alkyl, 2,2,2-trichloroethyl, silyl such as trimethylsilyl and t-butyidimethylsilyl, phenyl, ring substituted phenyl, e.g., 4-chlorophenyl, tolyl, and t-butylphenyl, phenyl ($C_{1-4}$) alkyl, ring substituted phenyl ($C_{1-4}$) alkyl, e.g., benzyl, 4-methoxybenzyl, 4-nitrobenzyl, benzyhydryl and trityl, methoxymethyl, 2,2,2-trichloroethoxycarbonyl, benzyloxymethyl ($C_{1-4}$) alkanoyloxy ($C_{1-4}$) alkyl such as acetoxymethyl, propionyloxymethyl, ($C_{2-4}$) alkenyl such as vinyl and allyl, unsubstituted or substituted phenyl ($C_{1-4}$) alkoxycarbonyl such as benzyloxycarbonyl and 4-nitrobenzyloxycarbonyl, and ($C_{2-4}$) alkenyloxycarbonyl such as allyoxycarbonyl. Particularly advantageous carboxyl-protecting groups are $C_{1-6}$ alkyl, benzyl, 4-nitrobenzyl, 2-nitrobenzyl, 2,4-dimethoxybenzyl, 4-methoxybenzyl and the like and, preferably, methyl or ethyl. Other suitable protecting groups are disclosed in "Protective Groups in Organic Synthesis", Theodora W. Greene (John Wiley & Sons, 1981), Chapter 5 for carboxyl, which is hereby incorporated by reference.

Fluorinating agents which can be employed in the present invention are, for example, N-fluoro-bis (phenylsulfonyl) amine (NFSi), 1-fluoro-4-hydroxy-1,4-diazoniabicyclo [2.2.2] octane bis tetrafluoroborate) (NFTh), 1-chloromethyl-4-fluoro-1,4-diazoniabicyclo[2.2.2]octane bis(tetrafluoroborate), 2-fluoro-3,3-dimethyl-2,3-dihydro-1, 2-benzisothiazole 1,1-dioxide, 1-fluoro-2,4,6-trimethylpyridinium triflate, 3,5-dichloro-1-fluoropyridinium triflate, 1-fluoropyridinium triflate, 1-fluoropyridinium tetraluoroborate, 1-fluoropyridinium pyridine heptafluorodiborate, N-fluoro-N-methyl-p-toluenesulfonamide, and the chiral fluorinating agent; (–)-N-fluoro 2,10-(3,3-dichlorocamphorsultam) [F. A. Davis et al., Tetrahedron Letters, pages 3971–3974, (1993)]. Both NFSI and NFTh are preferred and are available from Allied Signal, Buffalo Research Lab, 20 Peabody Street, Buffalo, N.Y.

Optically active salt-forming agents which can be employed in the present invention to resolve the racemic mixture into the individual enantiomers by conventional resolution methods such as fractional crystallization include resolving agents such as: (S)-(–)-α-methylbenzylamine, (R)-(+)-α-methylbenzylamine, (R) and (S) 2-phenylglycinol, (R) phenylephrine, D-phenylalaninol[(R) -2-amino-3-phenyl-1 -propanol], L-phenylalaninol[(S)-2-amino-3-phenyl-1 -propanol], (1R, 2S) norephedrine, (1S, 2R) norephedrine, (1R, 2S) ephedrine, (1S, 2R) ephedrine, (1R, 2S) N-methylephedrine, (1S, 2R) N-methylephedrine, (R)-cyclohexylethylamine, (S)-cyclohexylethylamine, (1R, 2R)-1,2-diaminocyclohexane, (1S, 2S)-1,2-diaminocyclohexane and the like.

The large conductance potassium channel modulator compound of Formula I may be prepared by various procedures and, preferably, by employing the intermediates of the formula

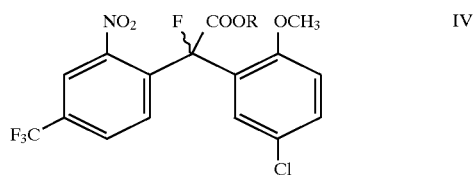

IV wherein R is as defined previously. Thus, the present invention provides a process for the preparation of the intermediates of Formula IV and also provides an improved process for the preparation of the compounds of Formula I.

REACTION SCHEME 1

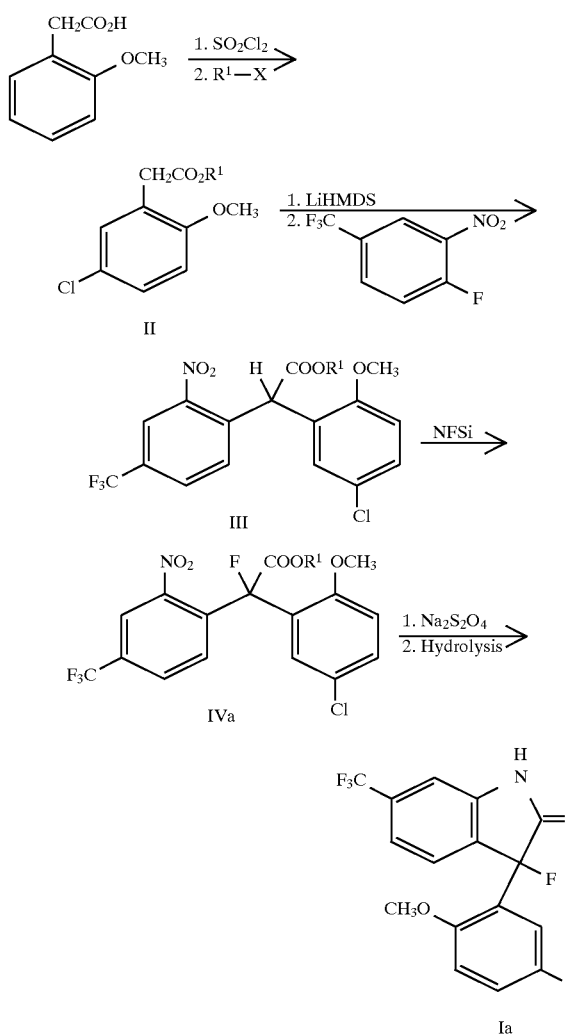

As illustrated in Reaction Scheme 1, the compounds of Formula IV may be prepared by chlorination of commercially available 2-methoxyphenylacetic acid with a chlorinating agent such as sulfuryl chloride in an organic solvent such as tetrahydrofuran and acetic acid and then converted to the carboxyl-protected compound of Formula II. Some of the carboxyl-protecting groups defined by $R^1$ which can be employed to block or protect the carboxylic acid moiety are described herein and others are well-known to those skilled in the art. For example, the methyl ester of Formula II was prepared from the acid using dimethyl sulfate and anhydrous potassium carbonate in an organic solvent such as acetonitrile or by using methanol with a catalytic amount of sulfuric acid. Reaction of the lithium enolate of the ester of Formula II with 4-fluoro-3-nitrobenzotrifluoride in the presence of one equivalent of additional lithium hexamethyldisilazane in THF at about −10° C. to −30° C. resulted in a solution of the lithium enolate of Formula III and acidic workup of the reaction provides the desired ester of Formula III. Advantageously, the racemic fluoro ester compound of Formula IVa may be prepared by treating the solution containing the lithium enolate of Formula III in situ with an electrophilic fluorinating agent such as described herein and preferably with N-fluoro-bis(phenylsulfonyl)amine to produce after an acidic workup the desired fluoro ester compound of Formula IVa.

When it is desired to prepare the racemic compound of Formula Ia as shown in Reaction Scheme 1, the fluoro ester of Formula IVa may be treated with reducing agents well-known in the art. Preferably, the reduction is carried out with sodium dithionite or another reducing agent which will reduce the nitro group without affecting the fluoro substituent. The resultant anilino-ester then spontaneously cyclized to provide the desired racemic 3-fluoro oxindole of Formula Ia.

REACTION SCHEME 2

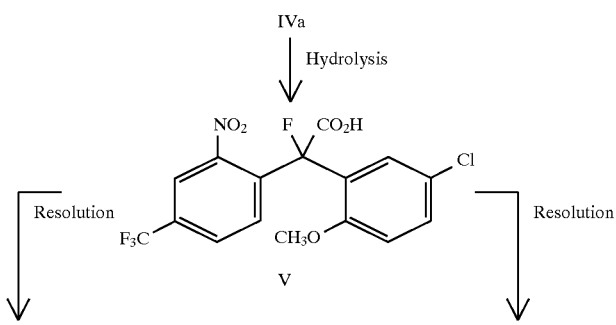

-continued
REACTION SCHEME 2

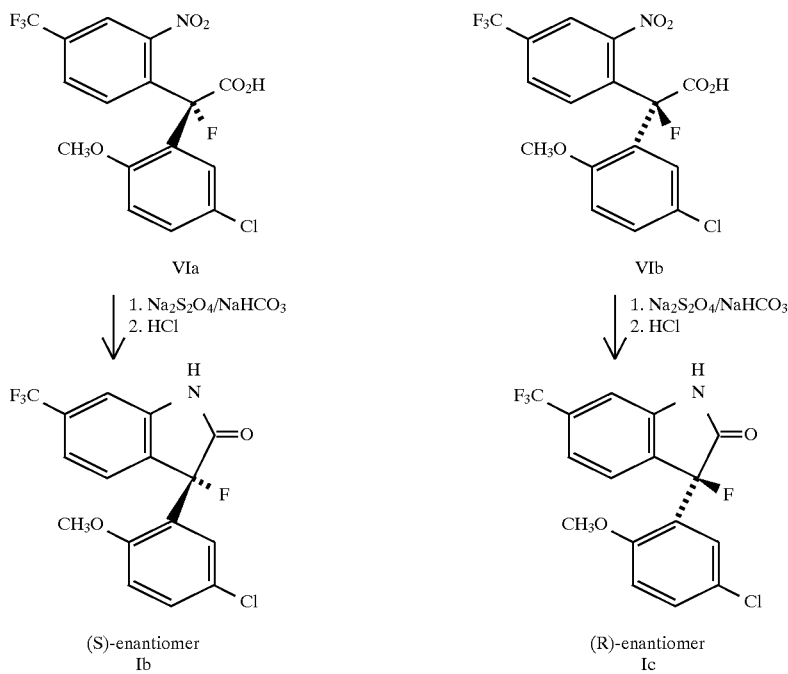

The substantially pure enantionmeric forms of 3-fluoro oxindole of Formulas Ib and Ic are advantageously prepared from the resolved acids of Formulas VIa and VIb, respectively, as shown in Reaction Scheme 2. The fluoro ester of Formula IVa is first hydrolyzed under basic conditions to provide the racemic acid of Formula V. The (S)-enantiomer of Formula Ib and the (R)-enantiomer of Formula Ic may be prepared from the corresponding racemic acid of Formula V by conventional resolution methods such as fractional crystallization after the introduction of a suitable salt-forming group. The resulting mixture of diastereoisomeric salts which is formed with an optically active salt-forming agent as described herein is separated and the separated resolved salt is converted to a compound of Formula Ib or Ic. Preferably, the salt-forming agents are (S)-α-methylbenzylamine and (R)-α-methylbenzylamine and the method of separation is by fractional crystallization. The resolution may be carried out in an inert organic solvent, and preferably, an alcohol solvent such as 2-propanol in which the resolved salt may crystallize from the solution.

When it is desired to prepare the substantially pure (S)-enantiomer of Formula Ib, the racemic acid of Formula V is first resolved using (S)-(α-methylbenzylamine and the resulting diastereoisomeric salt is converted to the optically active acid of Formula VIa which is then readily reduced and cyclized to provide the chiral compound of Formula Ib. By following the same sequence as above with the racemic acid of Formula V or, preferably, the enriched mother liquor derived from the resolution of the acid of Formula VIa and treating the acid with (R)-α-methylbenzylamine the substantially pure (R)-enantiomer of Formula Ic is produced from the corresponding separated diastereoisomeric salt.

In a preferred embodiment of the invention the compounds of Formula IV have the formula

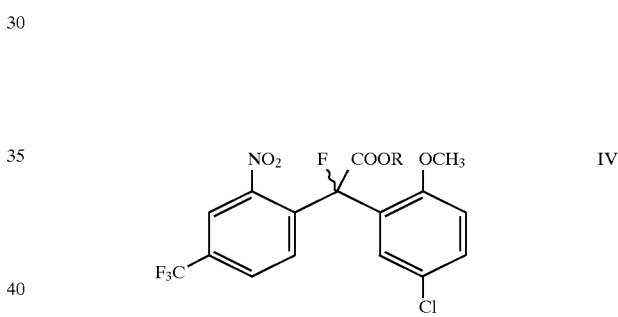

wherein the wavy bond (∼) represents the racemate, the (R)-enantiomer or the (S)-enantiomer; and R is hydrogen, a carboxyl-protecting group or a cation of an addition salt; or solvate thereof; with a educing agent to produce a compound of the formula

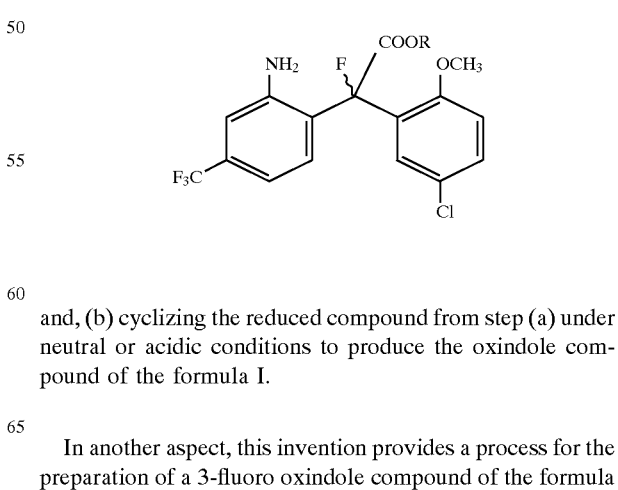

and, (b) cyclizing the reduced compound from step (a) under neutral or acidic conditions to produce the oxindole compound of the formula I.

In another aspect, this invention provides a process for the preparation of a 3-fluoro oxindole compound of the formula

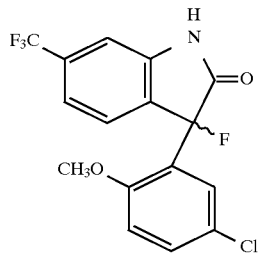

wherein the wavy bond (∼) represents the racemate, the (R)-enantiomer or the (S)-enantiomer, comprising the steps of:

(a) reducing a compound of the formula

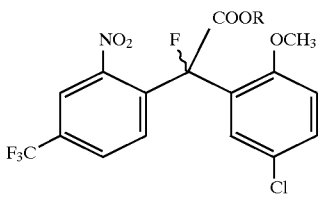

wherein the wavy bond (∼) represents the racemate, the (R)-enantiomer or the (S)-enantiomer and R is hydrogen, a carboxyl-protecting group or a cation of an addition salt; or solvate thereof; with a reducing agent to produce a compound of the formula

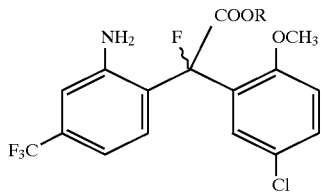

and, (b) cyclizing the reduced compound from step (a) to produce the oxindole compound of the formula I.

In a preferred embodiment, the invention provides a process for the preparation of the (S)-enantiomer of Formula Ib and the (R)-enantiomer of Formula Ic

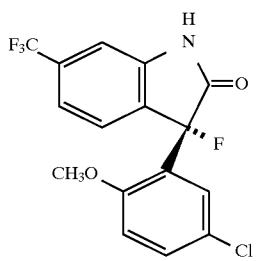 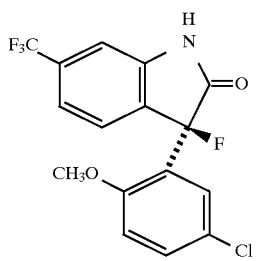

(S)-enantiomer    (R)-enantiomer
Ib                Ic

In still another aspect, this invention provides a process for preparing a racemic compound of the formula

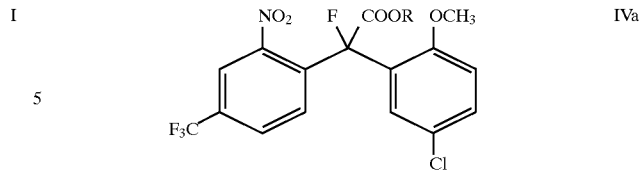

wherein R is hydrogen, a carboxyl-protecting group or a cation of an addition salt; or solvate thereof comprising the steps of (a) fluorinating a compound of the formula

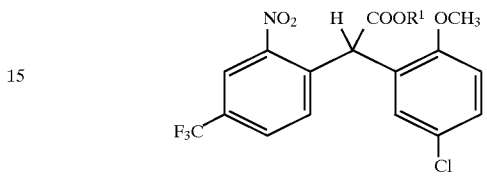

wherein $R^1$ is a carboxyl-protecting group with a fluorinating agent and (b) optionally, hydrolyzing the carboxyl-protecting group to produce said racemate compound wherein R is hydrogen or a cation of an addition salt; or solvate thereof.

In still a further aspect, this invention provides the resolution of the compound of Formula IVa with a chiral resolving agent to produce the corresponding (S)-enantiomer of Formula VIa and (R)-enantiomer of Formula VIb

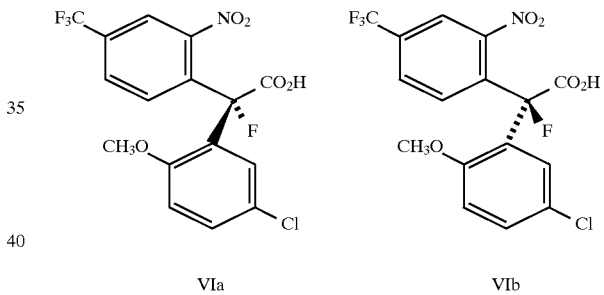

VIa                VIb

The compounds of Formula I are modulators of the large-conductance calcium-activated potassium channels and the utility thereof is more fully described by P. Hewawasam et al., in U.S. Pat. No. 5,565,483 issued on Oct. 15, 1996.

DESCRIPTION OF SPECIFIC EMBODIMENTS

In the following examples, all temperatures are given in degrees Centigrade. Melting points were recorded on a Gallenkamp capillary melting point apparatus and boiling points were measured at specific pressures (mm Hg) and both temperatures are uncorrected. Proton magnetic resonance ($^1$H NMR) and carbon magnetic resonance ($^{13}$C NMR) spectra were recorded on a Bruker AC 300. All spectra were determined in the solvents indicated and chemical shifts are reported in d units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Optical rotations $[\alpha]_D^{25}$ were determined on a Perkin-Elmer 241 polarimeter in the solvents indicated. Low resolution mass spectra (MS) and the apparent molecular (MH$^+$) was determined on a Finnigen TSQ 7000. The element analysis are reported as percent by weight. Capillary electrophoresis was determined on an Applied Biosystems 270A-HT CE System (72 cm×50 μm i.d. fused silica) at 30 °C. and 15 kV of voltage (80–90 μA) with a run buffer of 0.1M tauodeoxycholic acid in 0.1M sodium phosphate dibasic and detector set at 220 nm.

High pressure liquid chromatography (HPLC) was carried out with the sample dissolved in methanol and insjected on a YMC-Pack ODS-A, 150×6 mm, S-5 mm, 120 A column using (A) water w/0.1% trifluoroacetic acid and (B) acetonitrile w/0.1% trifluoroacetic acid as solvents with the detector set at a wavelength of 220 mm. The flow rate was set to 1.0 mL per minute and the column eluted with a gradient of 50% (B) to 90% (B) in 20 minutes; hold with 90% (B) for 5 minutes; step back to 50% (B) and hold for 5 minutes. Chiral HPLC was determined on a Chiracel-OD column.

It should also be evident to those skilled in the art that appropriate substitution of both the materials and methods disclosed herein will produce the examples illustrated below and those encompassed by the scope of this invention.

EXAMPLE 1

5-Chloro-2-methoxyphenylacetic acid, methyl ester
Step A

5-Chloro-2-methoxy phenylacetic acid

A flame dried three-necked 3-L round-bottomed flask, equipped with a septa, stirring bar, argon inlet, thermocouple and addition funnel capped with a septa, was vacuum/argon purged. The flask was charged with commercially available 2-methoxy phenylacetic acid (300 g, 1.81 mol) and anhydrous THF (2 L). The mixture was cooled to approximately –15° C. and stirred until the solution became homogeneous. Neat sulfuryl chloride (205 mL, 2.55 mol) was added dropwise via an additional funnel while stirring over an hour. The internal temperature was maintained below –5° C. (ranging between –15° and –5° C.). Immediately after the complete addition of sulfuryl chloride, HPLC analysis showed the reaction was complete. The reaction mixture was poured into cold water (16 L) with vigorous stirring. The resultant slurry was stirred for 3 hours and the white precipitate was collected by filtration, washed with water (2 L), air dried for about 24 h, and vacuum dried to afford 345.3 g (95% yield, 97% by HPLC) of the title compound as an off-white solid that was used without further purification in the next step.
Step B 5-Chloro-2-methoxyphenylacetic acid, methyl ester A flame dried three-necked 3-L round-bottomed flask, equipped with a stopper, mechanical stirrer, argon inlet, thermocouple and reflux condenser, was vacuum/argon purged. The flask was charged with the product obtained in Step A (345.0 g, 1.72 mol), anhydrous potassium carbonate (285 g, 2.06 mol) and anhydrous acetonitrile (1.7 L). To the resultant suspension was added dimethyl sulfate (200 mL, 2.11 mol) over 5 minutes with stirring and then heated to reflux at about 82° C. for 1.5 h to complete the esterification. The reaction mixture was cooled to room temperature and the excess dimethyl sulfate was quenched with triethylamine (70 mL). The resultant precipitate was filtered and washed with ethyl acetate (2 L) and the combined filtrate was concentrated on a rotary evaporator to afford a residue. This residue was partitioned between ethyl acetate (2 L) and 0.25N HCl (1 L). The organic layer was separated, washed with saturated sodium bicarbonate (2×2 L), 50% saturated sodium chloride solution (2 L) and dried over magnesium sulfate. The solution was filtered and the solvent was removed on a rotary evaporator to afford the crude ester as a dark brown oil. This residual oil was distilled under vacuum (170° C. at about 25 mm Hg) to afford 310 g (about 85% yield, 97% by HPLC) of the title compound as a viscous pale yellow oil.

EXAMPLE 2

5-Chloro-(α-fluoro-2-methoxy-α[2-nitro-4-(trifluoromethyl)-phenyl]benzeneacetic acid, methyl ester A four-necked 12-L round-bottomed flask, equipped with a septa, mechanical stirrer, argon inlet, thermocouple and 2-L addition funnel capped with a septa, was argon purged. The 5-chloro-2-methoxyphenylacetic acid, methyl ester from Example 1 (309.15 g, 1.44 mol) and 4-fluoro-3-nitrobenzotrifluoride (207.5 mL, 310.0 g, 1.48 mol) were transferred into the flask via a cannula and dissolved in anhydrous THF (750 mL). The clear light yellow solution was cooled in an acetone/dry ice bath to approximately –20° C. A solution of lithium hexamethyidisilazane in THF (1.0N, 3.16 L, 3.16 mol; dark orange-yellow in color) was transferred to the addition funnel and then added to the reaction mixture over a total of 1.5 hours. The internal temperature of the reaction mixture was maintained between –26° and –16° C. HPLC analysis after 10 minutes showed the reaction was complete. After a total of 40 minutes from the time of complete addition of lithium hexamethyldisilazane, a solution of N-fluoro-bis (phenylsulfonyl) amine (NFSi) (Accufluor™) (467.1 g, 1.48 mol, pink in color, Allied Signal, Buffalo Research Lab, 20 Peabody Street, Buffalo, N.Y.) in anhydrous THF (1.25 L) was cannulated into the reaction mixture over 20 minutes. The temperature of the reaction mixture was maintained at about –10° C. during the exothermic addition of the N-fluoro-bis(phenylsulfonyl) amine (Accufluor™) solution. The cooling bath was removed and the reaction mixture was allowed to warm to about 0° C. over about 1 hour, and HPLC analysis showed the reaction was complete. The reaction mixture was quenched with acetic acid (200 mL) resulting in an exotherm to 40° C., precipitation of the N-fluorobenzenesulfonide (Accufluor™) by-product and a color change from dark reddish-brown to orange. The mixture was diluted with water (4 L) and extracted with ethyl acetate (2×4 L). The combined organic layer was washed with 10% sodium carbonate (4×4 L), 50% saturated sodium chloride solution (1×4 L), 0.5N HCl (1×4 L) and saturated sodium chloride solution (1×4 L). The first two base washes, the 50% saturated sodium chloride solution wash and the HCl wash were back-extracted with ethyl acetate (2 L) and this organic layer was washed with saturated sodium chloride solution (1 L). The combined organic layers were then concentrated under vacuum at about 35° C. on a rotary evaporator to afford a semi-solid black residue (87% by HPLC). The residual oil was azeotropically dried with ethanol (2×500 mL) to remove water and ethyl acetate before crystallization. A 5-L flask equipped with a mechanical stirrer was charged with this residue and dissolved in ethanol (1.5 L) while stirring and heating in a boiling water bath. Heptane (2.6 L) was slowly added and the hot water bath was removed. The solution was allowed to slowly cool to room temperature (over 2 hours) to crystallize the product. After stirring for 16 hours, the suspension was cooled to 0° C. and stirred for 2.5 hours. The cold suspension was filtered, washed with cold 1:1 ethanol/heptane (1 L). The solid was air dried for about 2 h and then vacuum dried to afford 478.2 g of the title compound (78.8% yield, 99.3% by HPLC) as an off-white-peach colored solid.

m.p.=125°–127° C. (dec.).

Anal. calcd. for $C_{17}H_{12}O_5NClF_4$: C, 48.42; H, 2.87; N, 3.32; Cl, 8.41; F, 18.02

Found: C, 48.35; H, 2.69; N, 3.23;

Cl, 8.34; F, 18.49; $H_2O$, 0.60

EXAMPLE 3

(±)-3-(5-Chloro-2-methoxyphenyl)-3-fluoro-1,3-dihydro-6-(trifluoromethyl)-2H-indol-2-one A 250-mL 3-necked round-bottomed flask, equipped with a stir bar and thermocouple was charged with 5-chloro-α-fluoro-2-methoxy-α-[2-nitro-4-(trifluoromethyl)-phenyl]benzeneacetic acid, methyl ester (12.5 g, 29.64 mmol) and dissolved in THF (50 mL). Tetrabutylammonium chloride (0.84 g, 3.01 mmol) was dissolved in water (50 mL) and added to the THF solution. The reaction mixture was heated to about 60° C. and sodium dithionite (24.0 g, 118 mmol) was added portion wise as a solid over 75 minutes while stirring vigorously. After 5 minutes HPLC analysis showed that the reaction was complete. The reaction mixture was cooled to room temperature and the layers were separated. The aqueous phase was extracted with ethyl acetate (50 mL). The combined organic layers were treated with 1N methanolic HCl (15 mL) and heated to 55° C. for a few minutes. HPLC analysis showed that the cyclization was complete. THF and methanol were removed by concentrating on a rotary evaporator and the resultant residue was dissolved in ethyl acetate (100 mL) and hexane (100 mL). The organic layer was washed with 1N NaOH (2×50 mL), 1N HCl (2×50 mL), water (2×50 mL), saturated sodium chloride solution (50 mL), and dried over $MgSO_4$. The solution was then diluted with hexane (100 mL), treated with activated charcoal (5.0 g), heated to about 60° C. for 5 minutes, cooled to room temperature, filtered through Celite, and concentrated on a rotary evaporator to afford 10.54 g (99%) of crude product as a foam. This material was dissolved in ethanol (20 mL) and heated to reflux and water was slowly added (10 mL). Preferably, a seed crystal of the title compound was added resulting in crystallization of the product at about 75° C. The material was stirred for 16 hours at room temperature and then filtered, washed with 1:1 ethanol/water (40 mL), air and vacuum dried to afford 7.77 g of the title compound (73% yield, 97.5% by HPLC) as a white crystalline solid.

m.p.=165°–170° C. (dec.).

Anal. calcd. for $C_{16}H_{10}O_2NClF_4$: C, 53.43; H, 2.80; N, 3.89; Cl, 9.86; F, 21.13

Found: C, 53.36; H, 2.75; N, 3.77; Cl, 10.00; F, 21.03; $H_2O$, 0.10

EXAMPLE 4

5-Chloro-α-fluoro-2-methoxy-α-[2-nitro-4-(trifluoromethyl)-phenyl]benzeneacetic acid In a 3-necked 5-L round-bottomed flask, equipped with a mechanical stirrer and thermocouple, was suspended 5-chloro-(α-fluoro-2-methoxy-α-[2-nitro-4-(trifluoromethyl)phenyl]benzeneacetic acid, methyl ester (450 g, 1.067 mol) in methanol (2.0 L) and 1.0N aqueous sodium hydroxide (1.10 L, 1.10 mol). The reaction mixture was stirred for 4.5 hours at about 50° C. to complete the hydrolysis (determined by HPLC analysis). The reaction mixture was cooled to room temperature and concentrated on a rotary evaporator to remove most of the methanol. The residue was partitioned between tert-butylmethylether/hexane (1.2 L/0.5L) and water (1.4 L) and extracted. The organic layer was back-extracted with water (500 mL). The combined aqueous layers were cooled in an ice bath and while stirring vigorously, acidified with concentrated hydrochloric acid to about pH 1 (about 110 mL). Preferably, seed crystals of the title compound were added resulting in crystallization/precipitation of the product. The material was filtered after stirring for 3 hours at 0° C., air and vacuum dried overnight to afford 418.1 g of the title compound (96% yield when corrected for solvent, 99.6% by HPLC). A sample was recrystallized from toluene/hexane (1:1.25 at about 5 mL/g) to afford pure title compound.

EXAMPLE 5

(S)-(–)-5-Chloro-2-methoxy-α-fluoro-α-[2-nitro-4-(trifluoromethyl) phenyl]benzeneacetic acid, salt A 5-L three-necked round-bottomed flask, equipped with a mechanical stirrer and thermocouple, was charged with the racemic acid of Example 4 (392.87 g, 0.964 mol) and dissolved in isopropanol (2.0 L) to afford a light yellow solution. While stirring vigorously the reaction mixture was heated to 50° C. and then (S)-(α-methylbenzylamine was added over five minutes, causing the reaction tp turn slightly green in color. Heating was discontinued and a seed crystal was preferably added. Crystallization was observed within 15 minutes. The reaction mixture was cooled to room temperature over 2 hours while stirring and then the crystals were collected by filtration and washed with isopropanol (500 mL). After drying under vacuum, 208 g of the title compound as a 1:1 salt with (S)-α-methylbenzylamine (41% yield corrected for about 9% of 2-propanol as determined by 1H NMR; about 99.9% by HPLC) was obtained as a fluffy white solid. The product was found to be 99.3% enantiomerically pure as determined by capillary electrophoresis.

$[\alpha]_D^{25}$=–203° (c=1, MeOH).

Anal. calcd. for $C_{16}H_{10}O_5NClF_4 \cdot C_8H_{11}N \cdot C_3H_8O$: C, 55.06; H, 4.96; N, 4.76; Cl, 6.02; F, 12.90

Found: C, 54.94; H, 4.88; N, 4.69; Cl, 6.15; F, 12.91; $H_2O$, 0.11

EXAMPLE 6

(3S)-(+)-(5-Chloro-2-methoxyphenyl)-3-fluoro-1,3-dihydro-6-(trifluoromethyl)-2H-indol-2-one Step A (S)-(–)-5-Chloro-2-methoxy-α-fluoro-α-[2-nitro-4-(trifluoromethyl)phenyl]benzeneacetic acid The salt of Example 5 (8.83 g, 16.70 mmol) was dissolved in tert-butylmethylether (125 mL) and washed with 1N HCl (2×120 mL), water (120 mL) and saturated sodium chloride solution (120 mL). Concentrated the organic layer on a rotary evaporator to afford the free acid of the title compound in quantitative yield as an off-white solid.

Step B (3S)-(+)-(5-Chloro-2-methoxyphenyl)-3-fluoro-1,3-dihydro-6-(trifluoromethyl)-2H-indol-2-one The free acid obtained in Step A was dissolved in THF (42 mL) and then water was added (42 mL). Sodium bicarbonate (5.63 g, 66.83 mmol) was added slowly (evolution of gas is observed) to afford a homogeneous solution. Sodium dithionite (10.32 g, 50.41 mmol) was added portion wise as a solid over 60 minutes while stirring vigorously (evolution of gas is observed). HPLC analysis after 15 minutes showed the reaction was complete. The reaction mixture was diluted with saturated sodium chloride solution (42 mL) and ethyl acetate (42 mL) and the layers were separated. The organic layer was treated with 1N methanolic HCl (17 mL) and heated to 60° C. for 5 minutes and cooled slowly to room temperature. The reaction mixture was concentrated on a rotary evaporator and the resultant residue was partitioned between ethyl acetate (100 mL) and water (100 mL). The organic layer was washed with saturated sodium bicarbonate solution (2×100 mL) and concentrated on a rotary evaporator to afford 5.53 g (92%) of crude product as a yellow semi-solid. This material was dissolved in ethanol (24 mL) and heated to reflux and water was slowly added (24 mL). Preferably, a seed crystal of the title compound was added resulting in crystallization of the product while still hot. The material was stirred for 2 hours at room temperature and filtered, washed with 1:3 ethanol/water (50 mL), air and vacuum dried to afford 4.95 g of the title compound (83% yield, 99% by HPLC) as a light yellow crystalline solid which can readily be decolorized with neutral charcoal.

m.p.=202° C. (dec.)

$[\alpha]_D^{25}$=+156° (c=1, MeOH).

The enantiomer was identical to the racemate of Example 3 with respect to $^1$H and $^{13}$C NMR, mass spectrum, IR and elemental analysis and was found to be 99.9% enantiomerically pure by chiral HPLC.

EXAMPLE 7

(R)-(+)-5-Chloro-2-methoxy-(α-fluoro-α-[2-nitro-4-(trifluoromethyl)-phenyl]benzeneacetic acid, salt The mother liquor obtained from the resolution in Example 5 with (S)-α-methylbenzylamine was concentrated on a rotary evaporator to dryness and the resulting residue was dissolved in tert-butylmethylether (about 1.2 L). The solution was washed with 1N HCl (2×500 mL). The organic layer was diluted with hexanes (about 500 mL) and extracted with 0.5N aqueous sodium hydroxide solution (2×500 mL). The organic layer was discarded. The aqueous layer was cooled to about 0° C. and slowly acidified from pH 11.4 to 1.0, with concentrated HCl (during the pH adjustment a seed crystal of the product was preferably added) while stirring vigorously. After stirring for about 1 hour at 0° C., the solid was filtered and washed with water to afford the acid as pale yellow solid (195 grams, about 49.5% yield when corrected for solvent).

A 2-L three-necked round-bottomed flask, equipped with a mechanical stirrer and thermocouple, was charged with the above obtained solid (195 g, 0.48 mol) and dissolved in isopropanol (600 mL) to afford a light yellow solution. While stirring vigorously the reaction mixture was heated to 50° C. and then (R)-α-methylbenzylamine was added over five minutes. Heating was discontinued and crystals started forming immediately. The reaction mixture was cooled to room temperature over 2 hours while stirring and then the crystals were collected by filtration and washed with isopropanol (300 mL). After drying under vacuum, 203 g of the title compound as a 1:1 salt with (R)-(α-methylbenzylamine (40 % yield corrected for about 12.7% of 2-propanol as determined by 1H NMR; about 99.9% by HPLC) was obtained as a fluffy white solid. The product was found to be 99.7% enantiomerically pure as determined by capillary electrophoresis.

$[\alpha]_D^{25}$=+204° (c=1, MeOH).

EXAMPLE 8

5 (3R)-(-)-(5-Chloro-2-methoxyphenyl)-3-fluoro-1,3-dihydro-6-(trifluoromethyl)-2H-indol-2-one Step A (R)-(+)-5-Chloro-2-methoxy-α-fluoro-a-[2-nitro-4-(trifluoromethyl)phenyl]benzeneacetic acid The salt obtained in Example 7 (12.24 g, 23.6 mmol) was dissolved in tert-butylmethylether (125 mL) and washed with 1N HCl (2×120 mL), water (120 mL) and saturated sodium chloride solution (120 mL). Concentrated the organic layer on a rotary evaporator to afford the free acid of the title compound in quantitative yield as an off-white solid.

Step B (3R)-(-)-(5-Chloro-2-methoxyphenyl)-3-fluoro-1,3-dihydro-6-(trifluoromethyl)-2H-indol-2-one The free acid obtained in Step A was dissolved in THF (60 mL) and then water was added (60 mL). Sodium bicarbonate (8.1 g, 96.2 mmol) was added slowly (evolution of gas is observed) to afford a homogeneous solution. Sodium dithionite (15.04 g, 73.47 mmol) was added portion wise as a solid over 60 minutes while stirring vigorously (evolution of gas is observed). HPLC analysis after 15 minutes showed the reaction was complete. The reaction mixture was diluted with saturated sodium chloride solution (60 mL) and ethyl acetate (60 mL) and the layers were separated. The organic layer was treated with 1N methanolic HCl (30 mL) and heated to 60 ° C. for 5 minutes and cooled slowly to room temperature. The reaction mixture was concentrated on a rotary evaporator and the resultant residue was partitioned between ethyl acetate (100 mL) and water (100 mL). The organic layer was washed with saturated sodium bicarbonate solution (2×100 mL) and concentrated on a rotary evaporator to afford 7.45 g (86%) of crude product as a yellow semi-solid. This material was dissolved in ethanol (32 mL) and heated to reflux and water was slowly added (20 mL). A seed crystal of the title compound was preferably added resulting in crystallization of the product while still hot. The material was stirred for 2 hours at room temperature and filtered, washed with 2:1 ethanol/water (20 mL), air and vacuum dried to afford 5.26 g of the title compound (61% yield, 99.6% by HPLC) as a light yellow crystalline solid which can readily be decolorized with neutral charcoal.

m.p.=203° C. (dec.).

$[\alpha]_D^{25}$=-158° (c=1, MeOH).

The enantiomer was identical to the racemate of Example 3 with respect to $^1$H and $^{13}$C NMR;, mass spectrum, IR and elemental analysis and was found to be 99.9% enantiomerically pure by chiral HPLC.

What is claimed is:

1. A process for preparing a racemate compound of the formula

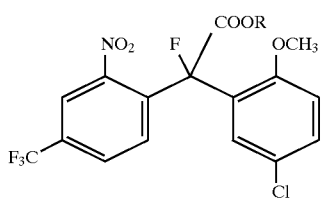

wherein R is hydrogen, a carboxyl-protecting group or a cation of an addition salt; or solvate thereof comprising the steps of (a) fluorinating a compound of formula

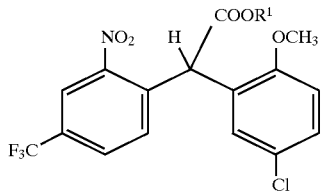

wherein $R^1$ is a carboxyl-protecting group with a fluorinating agent and (b) optionally, hydrolyzing the carboxyl-protecting group to produce said racemate compound wherein R is hydrogen or a cation of an addition salt; or solvate thereof.

2. A process of claim 1 wherein the fluorinating agent is N-fluoro-bis(phenylsulfonyl)amine.

3. A compound of the formula

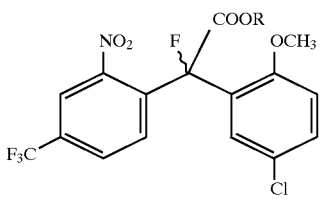

wherein the wavy bond (∼) represents the racemate, the (R)-enantiomer or the (S)-enantiomer; and R is hydrogen, a carboxyl-protecting group or a cation of an addition salt; or solvate thereof.

4. A compound of claim 3 wherein the compound is the racemate and R is hydrogen or a cation of an addition salt; or solvate thereof.

5. A compound of claim 3 wherein the compound is the (S)-enantiomer and R is hydrogen or a cation of an addition salt; or solvate thereof.

6. A compound of claim 3 wherein the compound is the (R)-enantiomer and R is hydrogen or an anion of a carboxylic acid addition salt; or solvate thereof.

7. The compound of claim 4 wherein R is hydrogen.
8. The compound of claim 5 wherein R is hydrogen.
9. The compound of claim 6 wherein R is hydrogen.

* * * * *